(12) United States Patent
Jassir et al.

(10) Patent No.: US 8,459,254 B1
(45) Date of Patent: Jun. 11, 2013

(54) NASAL DILATOR (76) Inventors: David Jassir, Davie, FL (US); Christine Jassir, Davie, FL (US)

(*) Notice: Subject to any disclaimer, the term of this patent is extended or adjusted under 35 U.S.C. 154(b) by 1429 days.

(21) Appl. No.: 12/072,832

(22) Filed: Feb. 28, 2008

(51) Int. Cl.
*A61M 15/00* (2006.01)
*A61M 16/00* (2006.01)
*A62B 7/00* (2006.01)
*A62B 9/00* (2006.01)
*A62B 18/00* (2006.01)

(52) U.S. Cl.
USPC .................................... 128/200.24

(58) Field of Classification Search
USPC ............ 128/200.24, 202.27, 206.11, 848, 128/200.26, 206.25, 207.17; 606/199, 204.45, 606/198; 24/3.1, 3.3, 3.12; 351/136, 158
See application file for complete search history.

(56) References Cited

U.S. PATENT DOCUMENTS

| | | | |
|---|---|---|---|
| 5,640,974 A | 6/1997 | Miller | |
| 6,006,746 A * | 12/1999 | Karell | 128/200.24 |
| 6,058,931 A | 5/2000 | Muchin | |
| 6,098,616 A * | 8/2000 | Lundy et al. | 128/200.24 |
| 6,216,282 B1 * | 4/2001 | Marzec | 2/452 |
| 6,266,827 B1 * | 7/2001 | Lampe et al. | 2/414 |
| 6,270,512 B1 | 8/2001 | Rittmann | |
| 6,860,263 B1 * | 3/2005 | Scoggins | 128/200.24 |
| 2001/0023695 A1 * | 9/2001 | Auriemma | 128/200.24 |
| 2003/0101542 A1 * | 6/2003 | Mackay et al. | 24/3.4 |
| 2007/0028917 A1 * | 2/2007 | Veeder | 128/200.24 |
| 2009/0025715 A1 * | 1/2009 | Sugden et al. | 128/200.24 |
| 2009/0183734 A1 * | 7/2009 | Kwok et al. | 128/200.24 |

* cited by examiner

*Primary Examiner* — Justine Yu
*Assistant Examiner* — Colin W Stuart
(74) *Attorney, Agent, or Firm* — Ronald V. Davidge (57) ABSTRACT A nasal dilator holds air passages within the nose of a person wearing the dilator by pulling outward on a pair of adhesive attachment pads attached to the person's cheeks at each side of his nose. In one version of the dilator, the pads are attached to opposite ends of a strap extending around the back of the person's head. In another version of the dilator, the pads are attached by straps to clamps, which are in turn attached to the sidepieces of eyeglasses also worn by the person.

3 Claims, 6 Drawing Sheets

NASAL DILATOR

BACKGROUND OF THE INVENTION

1. Field of the Invention

This invention relates to a device to hold nasal passages open during breathing'

2. Summary of the Background Information

The nasal valve is an area of the nasal passages that is considered to be the narrowest. During inhalation, negative pressures within the nasal valve may cause it to collapse, obstructing breathing through the nose. This obstruction has been associated with snoring during sleep and with sleep apnea.

To determine whether the nasal valve is the cause in a patient complaining to nasal congestion, a surgeon uses a method called the Cottle maneuver, in which the cheeks of the patient are distracted laterally from the sides of the nostrils. If the patient feels a subjective improvement in breathing, the test is considered to be a positive indication of such a problem with the nasal valve. While such a problem can be corrected surgically, many patients prefer not to have surgery, while others have medical conditions precluding elective surgery. When surgery is not used, a device may be prescribed to achieve the effects achieved during the use of the Cottle maneuver by pulling outward on the sides of the nose to hold the passages within the nasal valve open. While such a device may be worn during the day or night to relieve nasal congestion, it is hoped that the use of such a device at night will improve the conditions of snoring and sleep apnea.

The patent literature includes descriptions of a number of such devices having pads adhesively attached to the sides of the nose and pulled outward by a flexible spring member that extends across the bridge of the nose. For example, a flat spring member is formed into a U-shape by moving the ends of the device inward, with the pads being brought inward against the sides of the nose, and with the flexible spring member extending across the bridge of the nose. Since the pads are coated with an adhesive, they become adhesively attached to the sides of the nose as they are brought into contact with the nose. Then, when the ends of the device are released, the spring member attempts to restore itself outward, pulling the pads and the sides of the nose, attached to the pads, outward. An example of such a device is described in U.S. Pat. No. 6,058,931.

Alternately, the air passages within the nose can be held open by flexible device having ends extending upward within these passages from a central portion extending below the nose, as described in U.S. Pat. No. 6,270,512.

As described in U.S. Pat. No. 5,533,504, snoring may alternately be reduced or eliminated by holding the air passages within the nose shut, instead of open, with a device applying pressure to the sides of the nose through a pair of round pads, each of which is adjustably attached to a vertically oriented plate that is held against the face adjacent to the nose by a strap extending between the plates, around the back of the head. The distance between the plates is adjusted by a clamping mechanism extending under the nose.

U.S. Pat. No. 5,640,974 describes a kit for promoting effective breathing through the nasal passages. The kit includes a conventional nasal dilator, extending across the bridge of the nose, and a chin support member having an adhesive back for attachment to the user's face to hold his lips closed.

U.S. Pat. No. 6,336,456 describes a surgical mask of the type worn about the nose and face and tied around the head or ears. The inner surface mask includes a nasal dilator in the form of two attachment devices, each with a base upon which two layers of pressure-sensitive adhesive are applied for attachment to the sides of the nose and adjacent portions of the face. The mask is pinched inward toward the sides of the nose and adjacent portions of the face to attach the mask to the nose and adjacent portions of the face. When the pinching force is removed, the mask attempts to return to an initial position, moving the skin and muscles of the sides of the nose and adjacent face portions so that the nasal passages are opened.

What is needed is a device holding the nasal passages of a user open while providing comfort through attachment to the head of the user without a section of the device extending across the bridge of the nose of the user.

SUMMARY OF THE INVENTION

In accordance with one aspect of the invention, apparatus for dilating air passages within the nose of a person wearing the apparatus is provided, with the apparatus including first and second end portions and an attachment structure. Each of the first and second end portions includes a strap portion, which has a distal end and a proximal end, and an adhesive attachment pad, which has an inner surface at least partly coated with a pressure-sensitive adhesive, attached to the distal end of the strap portion. The attachment structure, which is attached to extend between the proximal ends of the first and second end portions, holds the first end portion to extend along the right side of the wearer's face, with the inner surface of the attachment pad within the first end portion adhesively attached to the wearer's right cheek adjacent a right side of the nose The attachment structure additionally holds the second end portion to extend along the left side of the wearer's face, with the inner surface of the attachment pad within the second end portion adhesively attached to the wearer's left cheek, adjacent a left side of the nose.

Preferably, the distal end of each strap portion is formed into a loop extending through a slot within the adhesive attachment pad. For example, the strap portion includes an attachment surface to which the end of the strap portion is attached to form the loop at a variable location, establishing a variable overall length of the strap portion In a first embodiment of the invention, the attachment structure includes a connecting strap portion extending between proximal ends of the first and second end portions, around the back of the wearer's head. A kit may be provided for the first embodiment of the invention, with the kit including a number of adhesive attachment pads and the support strap, including the end portions.

In a second embodiment of the invention, the attachment structure includes a pair of clamps for attachment to the sidepieces of a pair of eyeglasses worn by the person additionally wearing the apparatus. The first and second end portions are each attached to one of the clamps. A kit may be provided for the second embodiment of the invention, with the kit including a number of adhesive attachment pads and the two end portions, each of which is attached to one of the clamps. For example, each of the clamps may include a bracket forming a trough in which the sidepiece of the pair of glasses is held by a clamping screw. Alternately, each of the clamps includes a flexible tube, with the end portion attached to the rear end of the tube, and with the front end of the tube held against a surface of the eyeglasses at the front of the sidepiece. The flexible tube may hold a number of beads providing for stiffness in compression while allowing flexure as the flexible tube is slid into place over the earpiece of the eyeglasses.

DETAILED DESCRIPTION OF THE INVENTION

Figure 1:
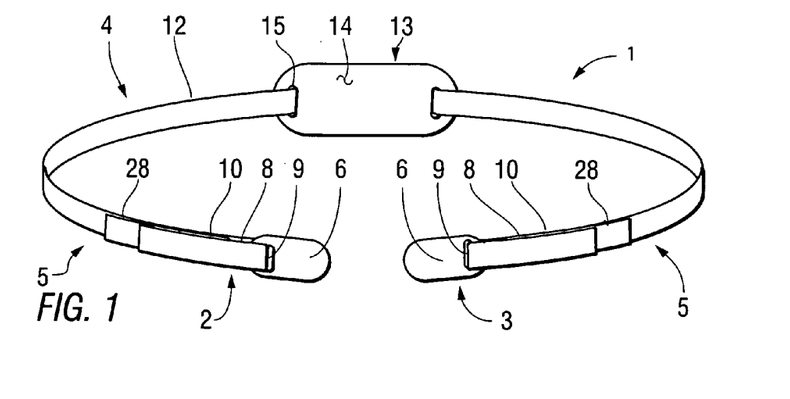
FIG. 1 is a perspective view of s nasal dilator built in accordance with a first embodiment of the invention.

FIG. 1 is a perspective view of a nasal dilator 1, built in accordance with a first embodiment of the invention to include a first end portion 2, a second end portion 3, a connecting strap portion 4, extending between proximal ends 5 of the end portions 2, 3, and an adhesive attachment pad 6, attached to each of the end portions 2, 3 by means of a loop 8 formed at a distal end 9 of a strap portion 10 within the end portion 2, 3. In the example of FIG. 1, the strap portions 10 and the connecting strap portion 4 are formed as portions of a support strap 12 configured to extend around the back of a person wearing the nasal dilator 1, with the adhesive attachment pads 6 attached to his cheeks adjacent each side of his nose. The nasal dilator 1 optionally further includes a support pad 13 attached to the connecting strap portion 4, with the support pad 13 being composed of a material, such as an elastomeric material, having surfaces 14 that resist sliding on adjacent surfaces. For example, the support pad 13 includes a pair of slots 15, through which the connecting strap portion 4 extends, with properties of the surfaces 14 preventing sliding of the support pad 13 on the wearer's hair and further preventing sliding to the support pad 13 on the connecting strap portion 4.

Figures 2, 4:
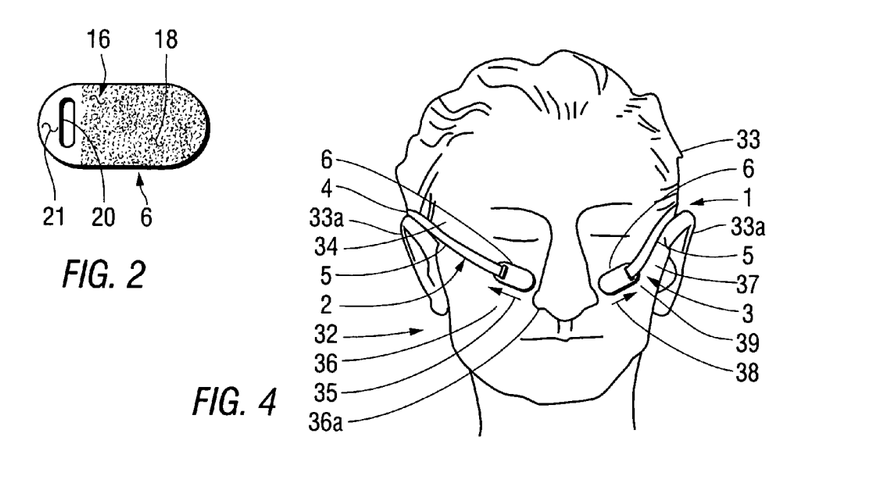
FIG. 2 is a rear elevation of an adhesive attachment pad within the nasal dilator of FIG. 1.
FIG. 4 is a fragmentary prospective view of a person wearing the nasal dilator of FIG. 1.

FIG. 2 is a rear elevation of one of the adhesive attachment pads 6, showing an inner surface 16 thereof held in contact with the user's face by means of an adhesive coating 18 applied to a portion of this surface 16. The adhesive attachment pad 6 includes a slot 20 that is used for attachment to the loop 8 within either of the end portions 2, 3. For example, the adhesive coating 18 is not applied to a surface 21 that will contact the loop 8, so that the attachment of the adhesive attachment pad 6 to the loop 8 and an adjustment of a length of the end portion 2, 3 is not complicated by contact between the loop 8 and the pressure sensitive adhesive coating 18. The adhesive attachment pad 6 may be composed of a suitably coated card stock.

Figure 3:
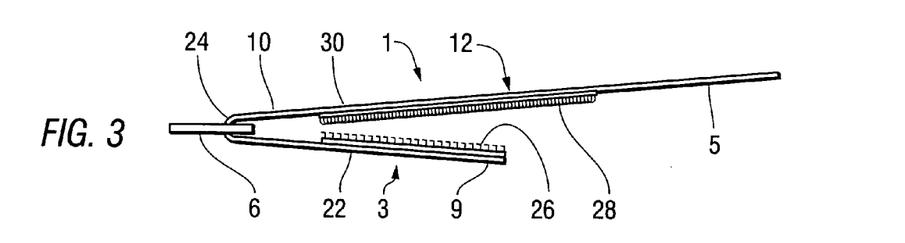
FIG. 3 is a fragmentary plan view of the nasal dilator of FIG. 1.

FIG. 3 is a fragmentary plan view of the nasal dilator 1, showing the second end portion 3 with the strap portion 10 therein extending through the slot 20 (shown in FIG. 2), so that the adhesive attachment pad 6 will pivot about a bend 24 within strap portion 10 of the second end portion 3. The strap portion 10 is provided with a first closure element 26 and a second closure element 28, configured to engage the first closure element 26, so that the distal end 9 of the strap portion 10 can be fastened to the strap portion 10 at a variable location 30 with this bend 24 being formed as the closure elements 26, 28 are brought together to form the loop 8 (shown in FIG. 1). For example, the first closure element 26 is the hook element, while the second closure element 28 is the loop element within a hook-and-loop fastener system, such as a VEL-CRO® fastener system. The actual location 30 is varied along the length of the strap portion 10 to determine the overall length of the second end portion 3.

FIG. 4 is a fragmentary perspective view of a wearer 32 wearing the nasal dilator 1, with the connecting strap portion 4, extending behind the head 33 and, preferably over the ears 33a of the wearer 32, between the proximal ends 5 of the first and second end portions 2, 3. The first end portion 2 extends along the right side 34 of the wearer's face to apply a tension force in the direction of arrow 35 to the adhesive attachment pad 6 within the first end portion 2, which is adhesively attached to the right cheek 36 of the wearer 32 adjacent his nose 36a. The second end portion 2 extends along the left side 37 of the wearer's face to apply a tension force in the direction of arrow 38 to the adhesive attachment pad 6 within the second end portion 3, which is adhesively attached to the left cheek 39 of the wearer 32

Figure 5:
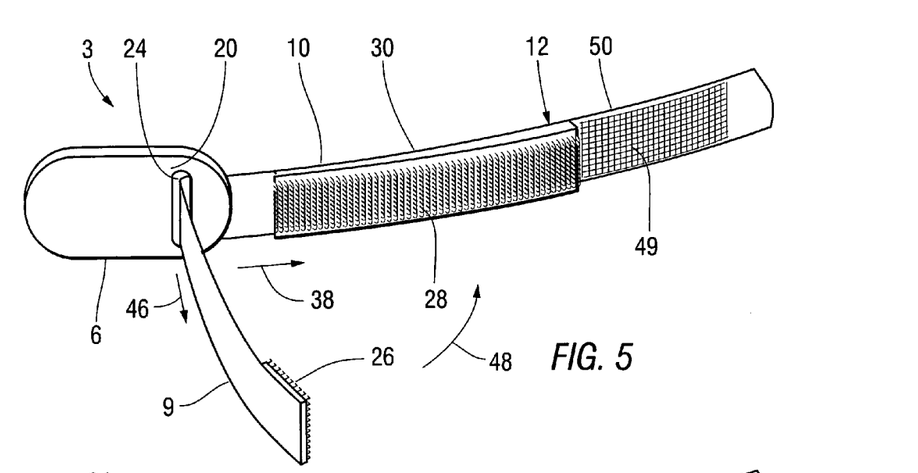
FIG. 5 is a fragmentary perspective view of the nasal dilator of FIG. 1, showing the attachment of an adhesive attachment pad therein and a tensioning adjustment.

FIG. 5 is a fragmentary perspective view of the second end portion 3, showing the attachment of an adhesive attachment pad 6 therein and a tensioning adjustment determining the force applied to the adhesive attachment pad 6 by the strap portion 10, so that a suitable shear force is applied to the right cheek 39 (shown in FIG. 4), acting in the direction of arrow 38. The process of attaching the adhesive attachment pad 6 to the strap portion 10 begins with pushing and pulling the distal end 9 of the strap portion 10 outward, in the direction of arrow 46, through the slot 20 within the adhesive attachment pad 6, beginning the formation of the bend 24 within the strap portion 10. The distances through which the distal end 9 of the strap portion 10 is pulled through the slot 20 determines the length of the second end portion 3, which in turn, together with the length of the first end portion 2 (shown in FIG. 1), determines the placement position of the adhesive attachment pads 6 on the cheeks 35, 39 of the wearer 32 (shown in FIG. 4) and the tension force applied by the strap portion 10 to the adhesive attachment pad 14. After distal end 9 is pulled through a slot 20, the distal end 9 is moved inward, in the direction of arrow 48, so that the closure elements 26, 28 engage one another. Preferably, the closure elements 26, 28 are configured to strongly resist separation by shear, so that the tension force applied to the adhesive attachment pad 6 in the direction of arrow 38 is maintained, but to yield to separation by normal forces as these elements 26, 28 are pulled apart, so that this tension force can be easily adjusted.

In a first version of the nasal dilator 1, the support strap 12 is composed of a material that resists tensile deformation while being easily bent. Examples of such a material are fabric ribbons and thin plastic film ribbons, composed of materials such as polyethylene terephthalate, With this version, the tension force applied by the support strap 12 to each of the adhesive attachment pads 14 is generally established by compressing portions of the sides 34, 37 of the face of the user 32.

In a second version of the nasal dilator 1, the support strap 12 is provided with elasticity, allowing relatively substantial lengthening in response to the application of a tension force. For example, the support strap 12 may be composed of an elastic fabric material extending along its length. Alternately, one or more sections of elastic fabric material may form portion(s) of the length of the support strap 12, with the remaining portion(s) thereof being formed, for example, by section(s) of a relatively non-extensible fabric ribbon. As shown in FIG. 5, one or more elastic sections 49 may be incorporated within the portion 50 of the support strap 12 extending between the two bends 24.

Figure 6:
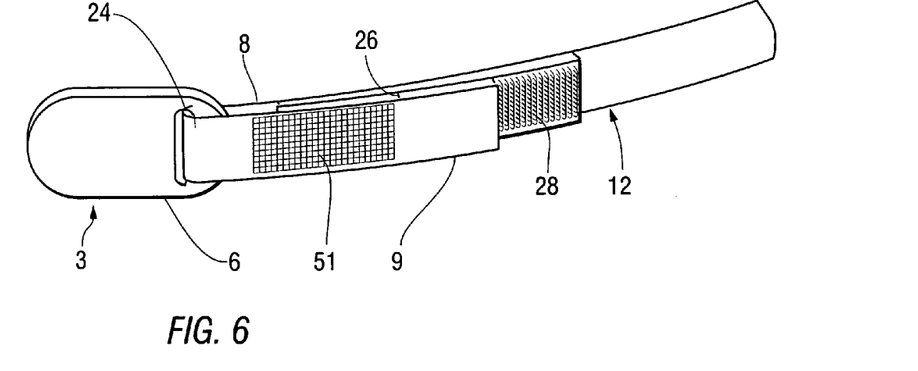
FIG. 6 is a fragmentary perspective view of the nasal dilator of FIG. 1, showing an alternative placement of an elastic member therein.

FIG. 6 is a fragmentary perspective view of the second end portion 3, showing the closure elements 26, 28 attached to one another, with an elastic section 51 being placed adjacent the distal end 9 of the strap portion 10. The elastic section 9 may alternatively extend around the bend 24, along the entire length of the strap portion 10 between the closure elements 26, 28.

While the second end portion 3 has been described in detail in reference to FIGS. 3, 5, and 6, it is understood that the first end portion 2 includes similar features.

Figure 7:
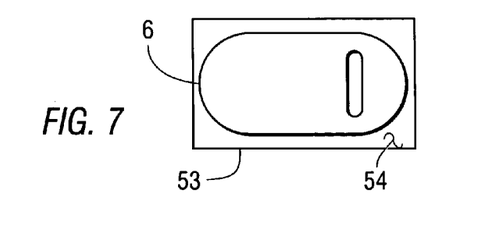
FIG. 7 is a plan view of an adhesive attachment pad, as provided for use within the nasal dilator of FIG. 1.

FIG. 7 is a plan view of the adhesive attachment pad 6, as provided for use within the nasal dilator 1. A release liner 53 is attached to the rear surface 16 (shown in FIG. 2), being held in place by the adhesive 18 and protecting this adhesive 18 from becoming dirty or from adhering to other objects before attachment to the face 34 of the user 32 (shown in FIG. 4). The release liner 53 includes a surface 54 that is easily peeled away from the adhesive attachment pad 6 before the adhesive attachment pad 6 is used.

Figure 8:
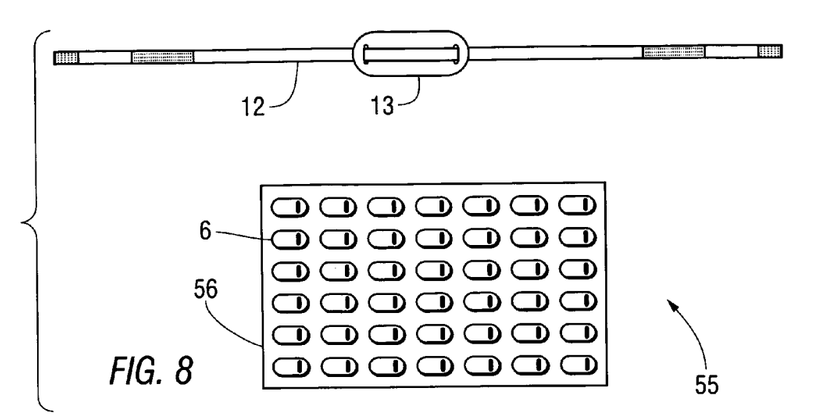
FIG. 8 is a plan view of elements within a kit provided to make the nasal dilator of FIG. 1.

FIG. 8 is a plan view of a kit 55 provided to make the nasal dilator 1. The kit 55 includes the support strap 12, optionally having the support pad 13, and a number of adhesive attachment pads 6, that are used as replacements providing renewed adhesive surfaces 18 as needed for continued usage of the nasal dilator 1. In the example of FIG. 8, the adhesive attachment pads 6 are provided as an array attached to a release liner sheet 56. In this form, individual adhesive attachment pads 6 are easily peeled away from the release liner sheet 56.

Figure 9:
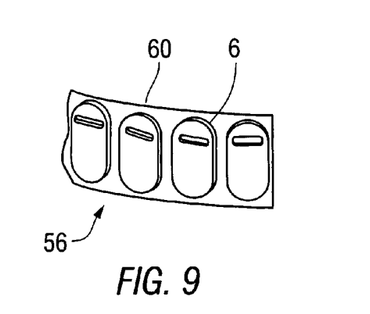
FIG. 9 is a fragmentary perspective view of an alternative assembly providing adhesive attachment pads for use within the nasal dilator of FIG. 1.

FIG. 9 is a fragmentary perspective view of an alternative assembly 58 for providing a number of adhesive attachment pads 6 for use within the nasal dilator 1, with the adhesive attachment pads 6 being attached to a tape 60 formed of a release liner material. The tape 60 may be wrapped into a spiral shape for convenient packaging.

Thus, a number of adhesive attachment pads 6 are packaged for sale, either as a part of a kit containing the support strap 12, or for separate sale as replacement parts for the nasal dilator 1, with the adhesive attachment pads 6 being attached to individual release liners 53, as shown in FIG. 7, to a release liner sheet 56 in the form of an array, as shown in FIG. 8, or to a release liner tape 60, as shown in FIG. 9.

Figure 10:
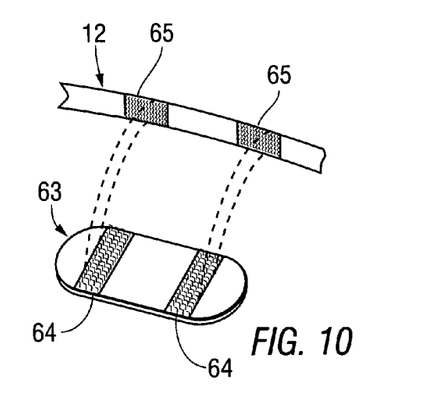
FIG. 10 is a perspective view of an alternate support pad, shown in an exploded relationship with a portion of a support strap within the nasal dilator of FIG. 1.

FIG. 10 is a perspective view of an alternate support pad 63, shown in an exploded relationship with a portion of the strap 12. In the example of FIG. 1, a support pad 13 is attached to the strap 12 with the strap 12 extending through slots 16 in the support pad 13. Alternately, as shown in FIG. 10, a support pad 63 may be removably attached to the strap 12 and repositioned thereon using mating closure elements 64, 65, such as VELCRO® closure elements.

Figure 11:
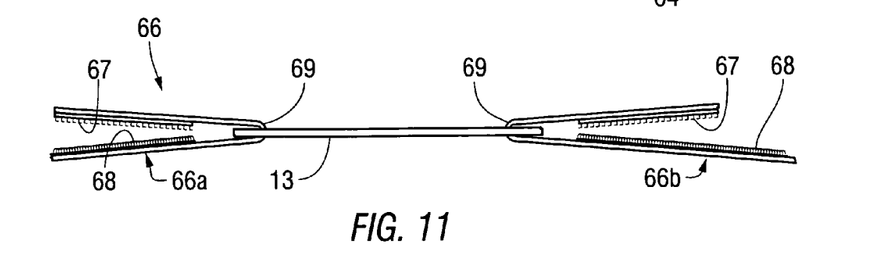
FIG. 11 is a fragmentary plan view of an alternative support strap for use within the nasal dilator of FIG. 1.

FIG. 11 is a fragmentary plan view of an alternative support strap 66, including a first support strap portion 66a and a second support strap portion 66b, each of which is provided with closure elements 67, 68, which are used to secure loops having bends 69 in the manner described above in reference to FIG. 3. these bends extend through the slots 15 (shown in FIG. 1) within the support pad 13. In this way, the overall length of the support strap can be adjusted from the rear by varying the location along the support strap portions 66a, 66b at which the bends 69 are formed. The alternative support strap 66 is used in place of the support strap 12 in the nasal dilator 1, shown in FIG. 1. While the alternative support strap 66 may be adjusted solely with in the back of the head, using the closure elements 67, 68, preferably the alternative support strap 66 additionally includes end portions 2, 3, as described above, allowing additional adjustments to be made at the front of the strap 66.

Figure 12:
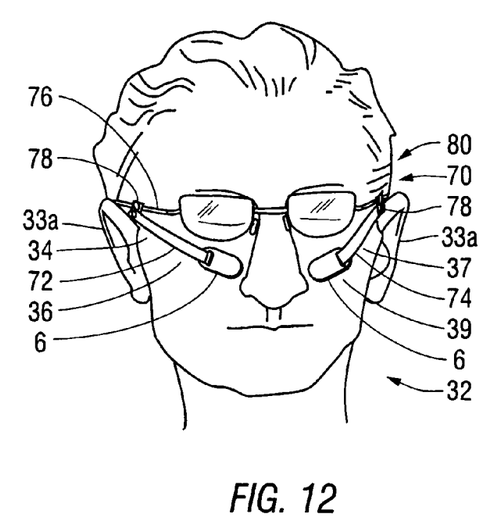
FIG. 12 is a fragmentary perspective view of a person wearing a nasal dilator built in accordance with a first version of a second embodiment of the invention.

FIG. 12 is a perspective view of the wearer 32 wearing a nasal dilator 70 built in accordance with a first version of a second embodiment of the invention to include a first end portion 72 and a second end portion 74, each of which is pivotally attached to a pair of eyeglasses 76 by means of a sliding clamp 78. Thus the eyeglasses 76 form a portion of an attachment structure 80 holding the first end portion 72 to extend along the right side 34 of the wearer's face with an adhesive attachment pad 6, as described above in reference to FIG. 2, being attached to the right cheek 36 of the wearer 32. Additionally, the second end portion 74 is held to extend along the left side 37 of the face of the wearer 32, with an adhesive attachment pad 6 being attached to the left cheek 39 of the wearer 32. Other aspects of the end portions 72, 74 are as described above regarding the second end portion 3, with reference being made to FIGS. 3, 5, and 6. For example, the nasal dilator 70 may be worn during the day to achieve a reduction in nasal congestion.

Figure 13:
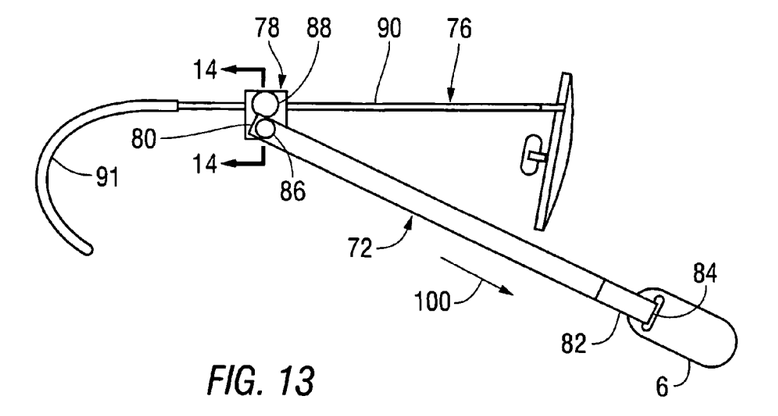
FIG. 13 is a side elevation of the nasal dilator of FIG. 12.

FIG. 13 is a side elevation of the nasal dilator 70, showing the proximal end 80 of the first end portion 72, pivotally attached to the eyeglasses 76 by means of the sliding clamp 78. An adhesive attachment pad 6 is attached to a loop 82, formed at the distal end 84 of the first end portion 72. The sliding clamp 78 includes a pivot screw 86 attaching the first end portion 72 to the sliding clamp 78 and a clamping screw 88, attaching the sliding clamp 78 to the right sidepiece 90 of the eyeglasses 76.

Figure 14:
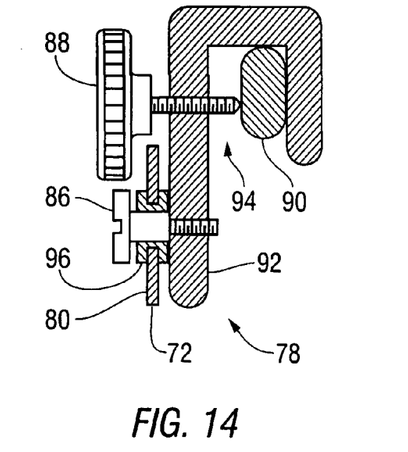
FIG. 14 is a cross-sectional front elevation of a sliding clamp within the nasal dilator of FIG. 12, taken as indicated by section-lines 14-14 in FIG. 13.

FIG. 14 is a cross-sectional front elevation of the sliding clamp 78, taken as indicated by section lines 14-14 in FIG. 13. The sliding clamp 78 includes a bracket 92 forming a trough 94, in which the right sidepiece 90 of the eyeglasses 76 is clamped by the clamping screw 88. Preferably, the trough 94 is large enough to accommodate a wide variety of eyeglass sidepieces. The proximal end 80 of the first end portion 72 includes an eyelet 96 for pivotal attachment using the pivot screw 86.

The location of the attachment pad 6 on the right cheek 36 of the user and the shear force applied by the adhesive attachment pad 6 may be varied both by sliding the sliding clamp 78 along the sidepiece 90, with the clamping screw 88 loosened to allow such movement, and by varying the location of the bend 98 forming the loop 82, as described above in reference to FIGS. 3, 5, and 6. The force applied by the first end portion 72 to the eyeglasses 76, acting downward and forward, in the direction of arrow 100, is resisted by contact between the earpiece 91 of the eyeglasses 76 and the ear 33a of the wearer 32.

While the above discussion has been directed largely to the first end portion 72 of the nasal dilator 70, it is understood that the second end portion 74 thereof has similar features that operate in a similar manner.

Figure 15:
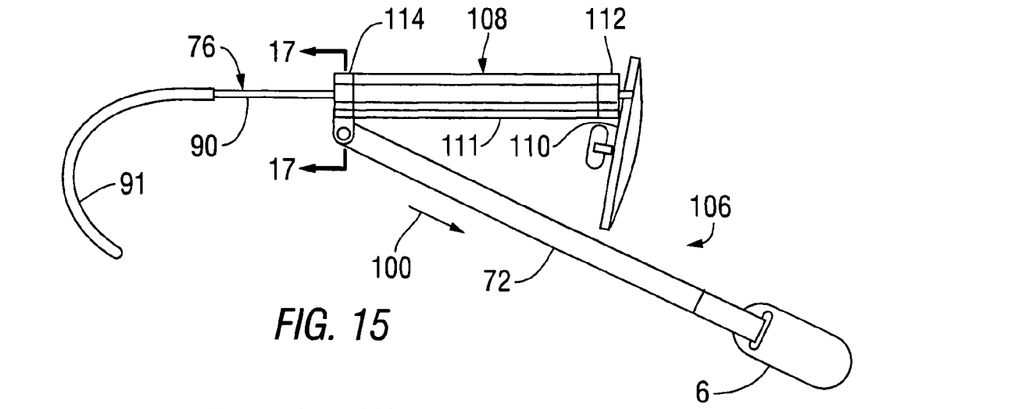
FIG. 15 is a side elevation of a nasal dilator built in accordance with a second version of the second embodiment of the invention.

FIG. 15 is a side elevation of a nasal dilator 106 built in accordance with a second version of the second embodiment of the invention to include a first end portion 72 and a second end portion 74 (shown in FIG. 12), which are described above, each of which is pivotally attached to the eyeglasses 76 by an alternative clamp 108. The alternative clamp 108 slides over the sidepiece 90 of the eyeglasses 76 to rest against a surface 110 at the front of the sidepiece 90.

Figure 16:
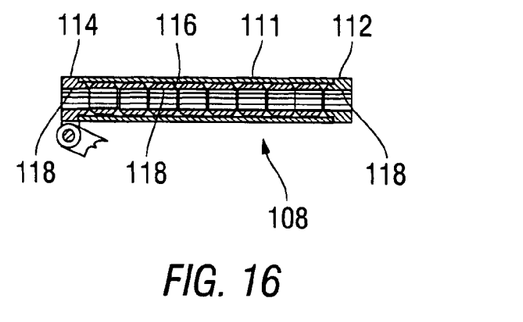
FIG. 16 is a cross-sectional side elevation of an alternative clamp in the nasal dilator of FIG. 15.

FIG. 16 is a cross-sectional side elevation of the alternative clamp 108, which includes a flexible tube 111 extending between a front end cap 112 and a rear end cap 114. The flexible tube 111 holds a number of beads 116, each of which includes an opening 118 for receiving the sidepiece 90 of the eyeglasses 76. The front end cap 112 and the rear end cap 114 include similar openings 118.

Figure 17:
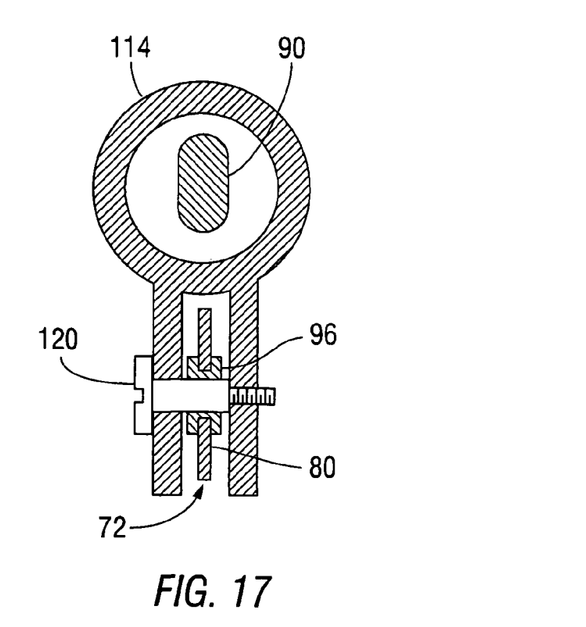
FIG. 17 is a transverse cross-sectional elevation of a rear end cap within the alternative clamp of FIG. 15, taken as indicated by section lines 17-17 in FIG. 15.

FIG. 17 is a transverse cross-sectional elevation of the rear end cap 114, taken as indicated by section lines 17-17 in FIG. 15. The rear end cap 114 includes a pivot screw 120, pivotally mounting the proximal end 80 of the first end portion 72, extending through the eyelet 96 therein.

When the alternative clamp 108 is placed over the front portion of the sidepiece 90, as shown in FIG. 15, a force derived from the shear force applied by the cheek 36 of the wearer 32 (shown in FIG. 12) is resisted by forces acting between adjacent beads 116, so that a reaction force is applied to the surface 110 at the front of the sidepiece 90, with this force then being transmitted through the sidepiece 90 to be resisted by contact between the earpiece 91 and the ear 33a of the wearer.

Figure 18:
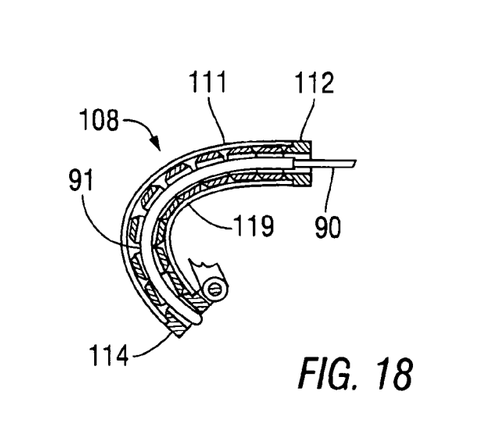
FIG. 18 is a cross-sectional side elevation showing the alternative clamp of FIG. 16 being pulled over an earpiece within a pair of eyeglasses.

FIG. 18 is a cross-sectional side elevation showing the alternative clamp 108 being pulled over the earpiece 91 to be slid onto the sidepiece 90, taking advantage of relative movement between adjacent beads 116. Alternately, the flexible tube 111 may be used without the beads 116 by controlling the material of which the tube 111 is composed and the thickness of its wall 119, so that the tube 111 can be curved over the earpiece 91, while sufficient stiffness is retained within the tube 111 to provide for transmission of the reaction force to the surface 110 as described above, without buckling the tube 111.

It is understood that the nasal dilator 106 additionally includes a second end portion 174 (shown in FIG. 12) and that this second end portion 174 is pivotally mounted on the opposite side of the eyeglasses 76 by means of a second alternative clamp 108, as described above.

Figure 19:
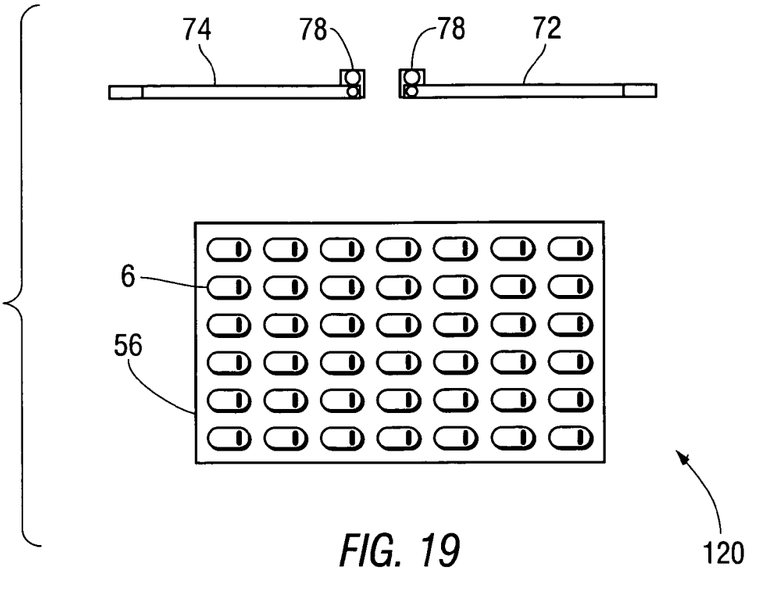
FIG. 19 is a plan view of a elements within a kit for making the nasal dilator of FIG. 12.

FIG. 19 is a plan view of a kit 120 provided to make the nasal dilator 70, consisting of a first end portion 72 and a second end portion 74, each of which is pivotally attached to a sliding clamp 78, together with an array of adhesive attachment pads 6, which are attached to a release liner sheet 56, as described above in reference to FIG. 8. Preferably, the end portions 72, 74 are identical, but are attached to the identical sliding clamps 78 in oppositely directed orientations, so the same sides of both the end portions 72, 74 and the sliding clamps 78 are directed outwardly from opposite sides of the eyeglasses 76 (shown in FIG. 12).

Figure 20:
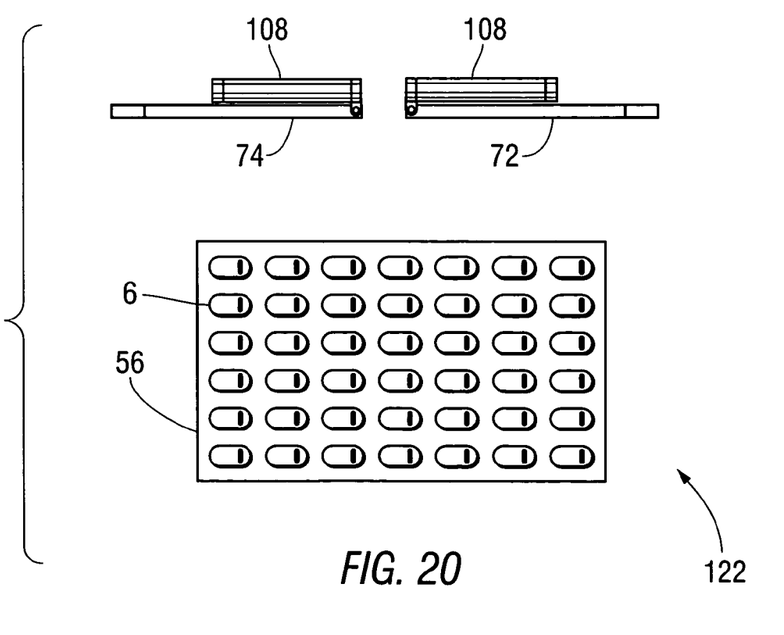
FIG. 20 is a plan view of elements within a kit for making the nasal dilator of FIG. 15.

FIG. 20 is a plan view of a kit 122 provided to make the nasal dilator 106, consisting of a first end portion 72, and a second end portion 74, each of which is attached to an alternative clamp 108. Again, the end portions 72, 74 are preferably identical, being attached to identical alternative clamps 108 in oppositely directed orientations.

While the invention has been shown and described in various embodiments and variations with some degree of particularity, it is understood that this description has been given only by way of example, and that many variations may be made without departing from the spirit and scope of the invention, which is described in the appended claims.

What is claimed is:

1. Apparatus for dilating air passages within a nose of a wearer, wherein
   the apparatus comprises a first and second end portions,
   the first end portion includes a first end strap, having a distal end and a proximal end, an adhesive attachment pad having an inner surface at least partly coated with a pressure-sensitive adhesive, attached to the distal end of the first end strap, and a first clamp configured to attach the proximal end of the first end portion to a first sidepiece within a pair of glasses,
   the second end portion includes a second end strap, having a distal end and a proximal end, an adhesive attachment pad having an inner surface at least partly coated with a pressure-sensitive adhesive, attached to the distal end of the second end strap, and a second clamp configured to attach the proximal end of the second end portion to a second sidepiece within the pair of glasses, and
   the first and second end portions are configured so that, when the pair of glasses worn by the wearer is attached to extend between the proximal ends of the first and second end portions, the first end portion is held to extend along the right side of a face of the wearer with the inner surface of the adhesive attachment pad of the first end portion adapted to be attached to a right cheek of the wearer adjacent a right side of the nose of the wearer, and holding the second end portion to extend along a left side of the face of the wearer with the inner surface of the adhesive attachment pad of the second end portion adapted to be attached to a left cheek of the wearer adjacent a left side of the nose of the wearer, and
   wherein each of the clamps includes, a front end cap having a hole for receiving a sidepiece from a pair of eyeglasses, a rear end cap having a hole for receiving the sidepiece, wherein the proximal end of one of the end portions is attached to the rear end cap; and a flexible tube, extending between the front and rear end caps, holding a plurality of beads, each having a hole for receiving the sidepiece.

2. The apparatus of claim 1, additionally comprising a plurality of the adhesive attachment pads, each attached to a single release liner sheet.

3. A kit forming apparatus for dilating air passages within the nose of a wearer, wherein the kit comprises:
   a plurality of adhesive attachment pads, each attached to a single release liner sheet, and each having an inner surface at least partly coated with a pressure-sensitive adhesive;

first and second clamps, each attachable to a sidepiece in a pair of eyeglasses;

a first end portion, including a strap portion with a proximal end attached to the first clamp and a distal end attachable to a location along the strap portion to form a loop holding one of the adhesive attachment pads, wherein, with the first clamp attached to a right sidepiece in a pair of eyeglasses worn by the wearer, the first end portion extends along the right side of a face of the wearer with the inner surface of an adhesive attachment pad within the plurality of adhesive attachment pads attached to the first end portion and adapted to be attached to a right cheek of the wearer adjacent a right side of the nose of the wearer; and a second end portion, including a strap portion with a proximal end attached to the second clamp and a distal end attachable to a location along the strap portion of the second end portion to form a loop holding one of the adhesive attachment pads, wherein, with the second clamp attached to a left sidepiece in a pair of eyeglasses worn by the wearer, the second end portion extends along the left side of a face of the wearer with the inner surface of an adhesive attachment pad within the plurality of adhesive attachment pads attached to the second end portion and adapted to be attached to a left cheek of the wearer adjacent a left side of the nose of the wearer, each of the clamps includes a front end cap having a hole for receiving a sidepiece from a pair of eyeglasses, a rear end cap having a hole for receiving the sidepiece, wherein the proximal end of one of the end portions is attached to the rear end cap; and a flexible tube extending between the front and rear end caps, holding a plurality of beads, each having a hole for receiving the sidepiece.

\* \* \* \* \*